United States Patent [19]

Bodicky

[11] 4,445,893
[45] May 1, 1984

[54] INFUSION APPARATUS

[75] Inventor: Raymond O. Bodicky, Oakville, Mo.

[73] Assignee: Sherwood Medical Company, St. Louis, Mo.

[21] Appl. No.: 377,761

[22] Filed: May 13, 1982

[51] Int. Cl.³ .............................................. A61M 5/00
[52] U.S. Cl. ..................................... 604/165; 604/177
[58] Field of Search ................................. 604/51–53, 604/93, 164–166, 168, 174, 177

[56] References Cited

U.S. PATENT DOCUMENTS

| | | | |
|---|---|---|---|
| 3,064,648 | 11/1962 | Bujan | 128/214 |
| 3,167,072 | 1/1965 | Stone et al. | 128/214 |
| 3,487,834 | 1/1970 | Smith, Jr. et al. | 604/165 X |
| 3,714,945 | 2/1973 | Stanley | 604/164 |
| 4,020,835 | 5/1977 | Nordstrom et al. | 128/214.4 |
| 4,082,094 | 4/1978 | Dailey | 128/214 R |
| 4,129,128 | 12/1978 | McFarlane | 128/133 |
| 4,193,399 | 3/1980 | Robinson | 604/168 |
| 4,209,015 | 6/1980 | Wicks | 604/174 X |
| 4,250,880 | 2/1981 | Gordon | 128/214 R |
| 4,253,463 | 3/1981 | Kim | 604/53 |
| 4,326,519 | 4/1982 | D'Alo et al. | 604/177 X |
| 4,353,369 | 10/1982 | Muetterties et al. | 604/53 X |
| 4,366,817 | 1/1983 | Thomas | 604/174 |
| 4,392,856 | 7/1983 | Lichtenstein | 604/177 |

Primary Examiner—C. Fred Rosenbaum
Assistant Examiner—Michelle N. Lester
Attorney, Agent, or Firm—Stanley N. Garber; Gregory E. Upchurch; William R. O'Meara

[57] ABSTRACT

An intravenous catheter placement device is provided which includes a catheter having a hub and a cannula. A winged stabilizing member is slideable onto the catheter hub. The catheter hub and stabilizer have cooperating keys and keyways to provide predetermined positioning of the stabilizer on the catheter. A needle introducer having a hub and a needle is provided with a cantilever in fixed relation with the needle bevel. The cantilever is located between the luer lock ears on the catheter hub when the introducer is inserted into the catheter to provide a predetermined orientation between the needle bevel and the wings of the stabilizer.

5 Claims, 6 Drawing Figures

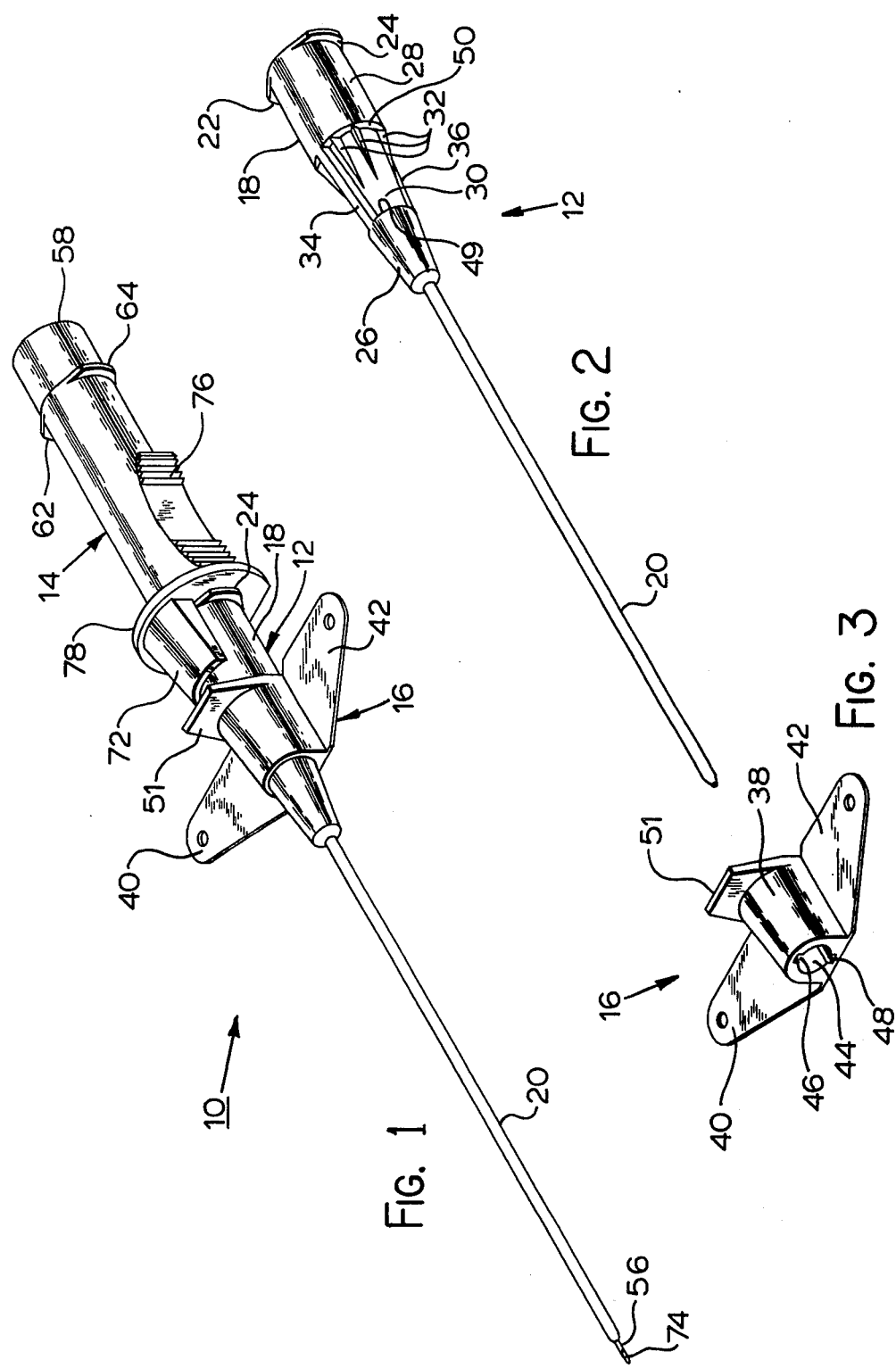

INFUSION APPARATUS

DESCRIPTION

1. Technical Field

This invention relates to infusion apparatus and more particularly to a catheter placement device.

2. Background Art

As is well known, catheter placement devices generally include a catheter having a cannula for insertion into a blood vessel, such as a vein of a patient, and a hub for coupling engagement with a tube adapter used to connect the catheter with a source of infusion liquid. A catheter introducer or needle assembly is used to introduce the catheter cannula into the vein. The needle is inserted through the catheter cannula with the pointed end of the needle extending beyond the distal end of the cannula so that both are readily introduced into the vein. Thereafter, the needle is removed from the catheter and the catheter is connected to the infusion liquid source.

The catheter hub may have a stabilizer or securing member with wings that can be sutured and/or taped to the patient for stabilizing the catheter and maintaining it immovable during infusion. Where such wings are integrally formed with the catheter hub, they are generally of rigid plastic material since the hub generally must be made of relatively rigid material to enable sufficient torque to be applied to it to ensure fluid-tight coupling with an adapter. Such rigid wings can be a discomfort to the patient because of rigid edges on the stabilizer. In some cases, relatively soft, more comfortable, plastic wings are placed on the catheter hub, however, connecting the wings with the hub is not always easily accomplished and such wings are generally subject to separation from the hub.

Another problem associated with certain catheter placement devices is that the introducer needle bevel at the pointed end is not automatically or obviously oriented in the desired position relative to the wing member where used, or the skin surface during venipuncture. This makes it necessary for the person effecting the venipuncture to closely examine the needle tip and determine that the bevel is in the correct or desired position with regard to the skin and maintain it in that position during insertion. It is generally preferred to introduce the needle and cannula into the vein with the needle bevel on top of the needle and facing away from the skin. In order to do this with some devices, careful examination of the tip and careful holding of the tip during venipuncture are required.

SUMMARY OF THE INVENTION

It is an object of the present invention to provide an improved catheter placement device which can be used with a securing member of resilient material or without a securing member if desired, wherein the bevel on the needle of the introducer is readily maintained in proper orientation, and wherein one or more of the above-mentioned problems of the prior art devices are overcome.

In accordance with one form of the present invention, an intravenous catheter placement device is provided which includes a catheter hub having a flexible cannula extending distally from the distal end of the catheter hub. The catheter hub has an alignment element for cooperation with an alignment element on a catheter securing member which may be made of relatively resilient material and have a pair of opposed wings and with an inner wall of the hub extending circumferentially continuously. In another aspect of the invention, a catheter introducer having a hub and needle is provided with an alignment member which, when the introducer is inserted into the catheter, hub cooperates with an alignment member on the catheter hub to predeterminately position the bevel of the needle relative to the hub and with the wings of a stabilizer when used.

These, as well as other objects and advantages of the present invention, will become more apparent from the following detailed description and drawings.

BRIEF DESCRIPTION OF THE DRAWINGS

FIG. 1 is a perspective view of an intravenous catheter placement device in accordance with a preferred embodiment of the present invention;

FIG. 2 is a perspective view of the catheter of FIG. 1;

FIG. 3 is a perspective view of the winged stabilizing member of FIG. 1;

BEST MODE FOR CARRYING OUT THE INVENTION

Figure 4:
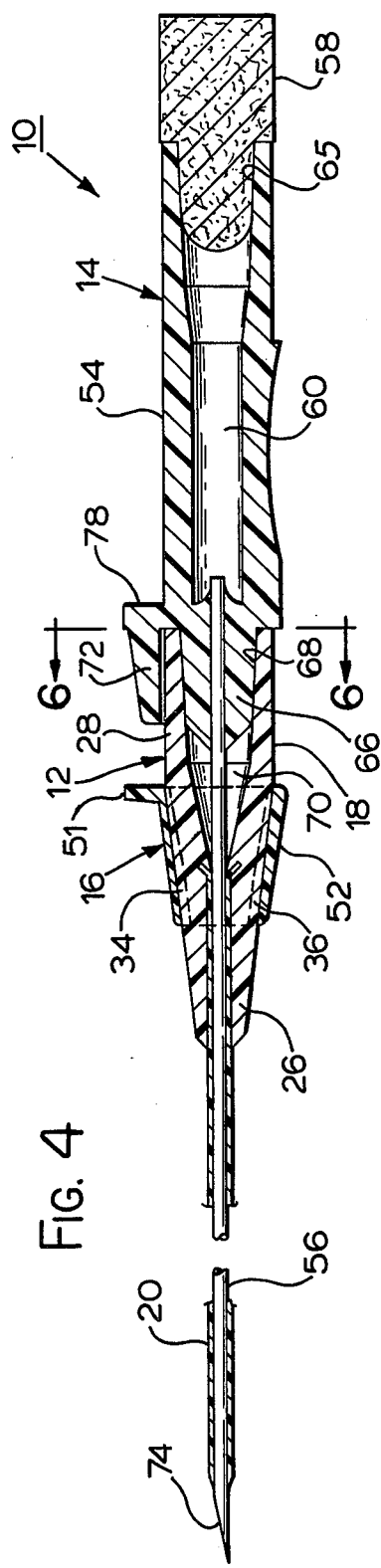
FIG. 4 is a side view in cross-section and on an enlarged scale of the device of FIG. 1.

Referring now to the drawings, and particularly to FIG. 1, an intravenous catheter placement device 10 is shown including an intravenous catheter 12, an introducer or needle assembly 14 for inserting the catheter into a blood vessel such as a vein of a patient, and a catheter stabilizing or securing member 16 for aiding in securing the device 10 in an operative position on the patient. The catheter 12 and stabilizing member 16 are shown independently in FIGS. 2 and 3, respectively.

The catheter 12, as best seen in FIGS. 2 and 4, includes a relatively rigid hub 18 and a relatively flexible catheter cannula 20 fixed to and extending distally from the distal end of hub 18. Hub 18 is preferably made of relatively rigid or hard plastic, for example, hard polypropylene, polycarbonate, or the like, so that it can be manually connected in fluid-tight connection with other devices without deformation. The cannula 20 is preferably made of a somewhat flexible plastic such as Teflon (fluoroethylenepropylene) or the like, and may be secured to hub 18, for example, by molding the hub about the proximal end of cannula 20 or by using a suitable cement. The hub 18 is molded or otherwise formed with a pair of conventional, opposed luer lock radial ears 22 and 24 at the proximal end of the hub. Ears 22 and 24, as is well known, can be threaded into a complementary luer lock coupling of a tube adapter (not shown) for connecting the catheter with an infusion set having a source of infusion liquid.

Hub 18 has a generally conical portion 26 that extends to the distal end, a generally cylindrical portion 28 at the proximal end, and a generally annular recess 30 intermediate the distal and proximal ends of hub 18. The recess 30 is formed in conical portion 26 and is provided with a finger-gripping or roughened surface that will resist slipping between the fingers when grasped, the roughened surface being provided for in the illustrated embodiment by a plurality of circumferentially spaced ribs 32 in recess 30. This roughened surface is useful when a stabilizer is not employed. When a stabilizer, such as stabilizer 16, is employed, it covers this roughened surface.

Hub 18 is also provided with a pair of alignment members or orienting keys 34 and 36 diametrically spaced apart and extending longitudinally or axially across the groove 30. Keys 34 and 36 serve as guide or aligning members for guiding the stabilizer 16 onto the hub 18 and predeterminately aligning or locating it in fixed relative position to the luer lock ears 22 and 24 which extend laterally outwardly from the opposite sides of the catheter hub 18.

If catheter 12 is employed without using stabilizer 16, adhesive tape may be applied directly over the hub 18 to secure it to the skin of the patient, such as on the arm of the patient. However, it is often desired to employ a stabilizer such as stabilizer 16 to aid in stabilizing and securing the catheter 12 to the patient.

Figure 5:
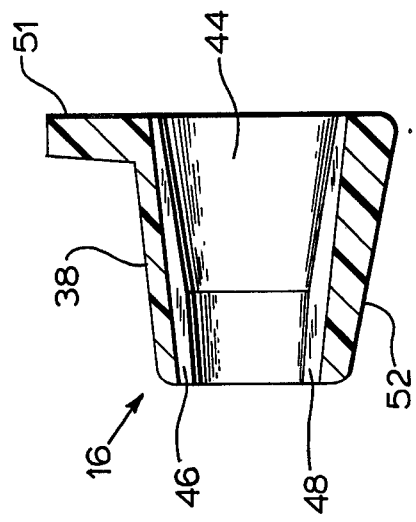
FIG. 5 is a side view in cross-section on an enlarged scale of the stabilizing device of FIG. 3.

Stabilizer 16 includes a main body portion 38 and a pair of opposed wings 40 and 42 integrally connected to and extending laterally outwardly from the opposite sides of the body portion 38. The body 38 has a circumferentially continuous central bore 44 extending through it, as best seen in FIGS. 4 and 5. A pair of diametrically opposite keyways 46 and 48 are provided which are complementary and cooperate with the keys 34 and 36 on the catheter hub 18 when the stabilizer 16 is inserted on the hub. In placing the stabilizer 16 on the hub 18, the cannula 20 may be moved through bore 44 and such that the upper keyway 46 receives the upper key 34 and the lower keyway 48 receives the lower key 36, and then the stabilizer is moved into the recess 30.

The stabilizer bore 44 is preferably sized such that the stabilizer 16 must be somewhat stretched as it is moved upwardly along the hub 18 and into the recess 30. When in place, stabilizer 16 is disposed between the opposed end walls, indicated at 49 and 50 (FIG. 2) of the recess. Preferably, the stabilizer 16 is molded from a suitable, somewhat elastic and pliable or supple material such as rubber or soft plastic, for example, a soft and somewhat elastic polyvinyl chloride may be used. The stabilizer 16 is also shown including suture holes and an integral upstanding tab 51 which may be pushed by the index finger while removing the introducer 14 with the thumb and second finger to thereby provide a one-hand procedure. As seen in FIG. 5, the bore 44 tapers outwardly toward the proximal end so that it generally conforms to the bottom surface of recess 30 and provides a snug and secure fit within the recess so that stabilizer 16 will not come off the catheter under normal conditions. Preferably, the diameters of the bore 44 at its distal and proximal ends are less than the outer diameters of walls 49 and 50, respectively, to ensure that the stabilizer will not move axially.

The stabilizer body portion 38 has an outer bottom wall 52, as seen in FIGS. 4 and 5, which is inclined at an angle to the longitudinal axis of the device 10 such that, when flat and parallel with the skin of the patient, the axis of the bore 44 will be inclined distally downwardly toward the skin. Both wings 40 and 42 are shown on the bottom of device 10 and have bottom surfaces which are in the same plane as wall 52 so that the bottom surface of the stabilizer is flat from one wing tip to the other and in the same plane. This provides a relatively large, flat surface area against the skin so that when these wings are held down, for example, by sutures passing through the skin and holes in the wings, and/or adhesive tape, the catheter 12 is securely held in place at a desired angle and location on the patient.

The introducer 14, as shown in FIGS. 1 and 4, includes a needle hub 54, an introducer needle 56 fixed to and extending distally from the distal end of hub 54, and a gas permeable, liquid impermeable, plug member 58 closing the proximal end of the hub. The needle 56 is of metal, preferably it is a stainless steel needle cannula. The needle hub 54 is preferably made of a relatively hard plastic such as the same plastic used to make hub 18 of the catheter 12. It is shown provided with a bore 60 communicating with the bore of the needle cannula 56. The needle hub 54 is provided with a pair of integral luer lock ears 62 and 64 at the proximal end of hub 64 (FIG. 1) which may be used with a luer lock coupling. The bore 60 has a proximal end portion indicated at 65 which is a tapered luer bore coupling adapted to receive a complementary luer slip coupling (not shown), for example, a syringe tip. Plug 58 is shown extending into the luer tapered connector bore portion 65 to prevent the flow of blood from the proximal end of bore 60 during venipuncture but to allow air to escape as the blood fills the needle hub.

The needle hub 54 is formed with a tapered connector 66 integrally formed at the distal end of the hub and which sealingly fits within a luer tapered connector bore portion 68 in the catheter hub bore indicated at 70. The catheter bore 70 communicates with the catheter cannula 20.

Figure 6:
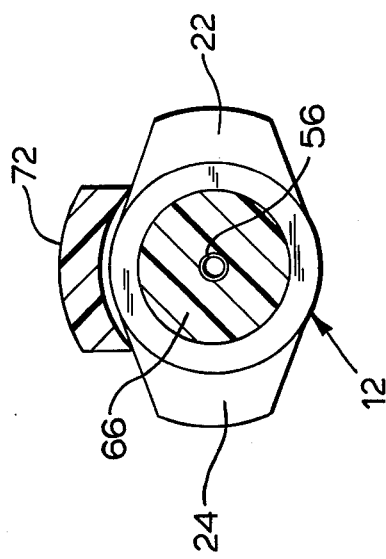
FIG. 6 is a cross-sectional view, on an enlarged scale, taken along the line 6—6 of FIG. 4.

The needle hub 54 also is provided with an alignment or orientation indicating member shown as a cantilever or axially extending portion 72 adjacent the distal end of the hub. Cantilever 72 extends distally over the connector portion 66 and the catheter hub 18. When the needle 56 is inserted through the catheter 12, the cantilever 72 passes between the ears 22 and 24 of the catheter hub 18, as is more clearly seen in FIG. 6. Needle 56 is fixed in the needle hub 54 such that the cantilever 72 and bevel 74 are in predetermined relation on the same side of the needle assembly. In this way, the ears 22 and 24 cooperate with the cantilever 72 to position the needle bevel 74 in predetermined relation with the catheter 12 and stabilizer 16. The needle assembly 14 cannot rotate because it is engaged between the ears 22 and 24. The orientation of the needle assembly 14 with catheter 12 is such that the face or plane of the bevel 74 is at the top of the needle 56, that is, the bevel extends distally and downwardly from a point proximally spaced from the tip of the needle 56, as best seen in FIG. 4.

Because the securing or stabilizing member 16 is in predetermined orientation with the catheter hub 18, the wings 40 and 42 are predeterminately positioned relative to the luer lock ears 22 and 24 of hub 18, and therefore also with the cantilever 72 and needle bevel 74. This provides the desired orientation between the bevel 74 of needle 56 and the plane of the wings 40 and 42 of stabilizer 16. A finger-grasping portion, indicated at 76 in FIG. 1, on the needle hub 54, provides an orientation feel relative to the cantilever 72 and the bevel 74. Thus, to the person inserting the infusion device 10 into the vein of the patient, the positions of the portion 76, cantilever 72, wings 40 and 42, and tab 51 provide positive indications that the needle bevel 74 is facing upwardly or on the top of the needle 56 (FIG. 4), as is generally desired by most persons who perform catheter insertions.

In use, with the device 10 held with the wings 40 and 42 generally parallel with the flesh, and the cantilever 72 and the tab 51 located on top of the device, the distal ends of needle 56 and cannula 20 are inserted into the patient. If the venipuncture is successful, blood will flow into the needle hub with air being displaced through the air permeable plug 58. The introducer hub 54 is preferably made of transparent plastic so that blood in the hub can be seen. While holding the stabilizer 16 and catheter 12 after a successful venipuncture, the introducer needle assembly 14 may be removed proximally from the catheter 12. A conventional, internally threaded luer lock coupler or tube adapter (not shown) may be then inserted onto the proximal end of hub 18 of the catheter and the ears 22 and 24 threaded into the threaded portion of the coupling to provide a secure, fluid-tight luer lock coupling between hub 18 and the adapter. The adapter may be part of an infusion set for introducing infusion liquid through the adapter, hub 18, and catheter cannula 20 into the vein of the patient. Since the catheter is inserted into the patient with the plane of wings 40 and 42 of the stabilizer generally parallel with the skin of the patient, the wings are simply placed flatwise down against the skin and sutured and/or taped in place while maintaining the distal end of the catheter cannula 20 disposed in the vein.

The infusion device or catheter placement device 10 may be assembled by the manufacturer in the condition shown in FIG. 1 and packaged in a sterile container ready for use. Such devices are generally for single use, that is, they are discarded after using with one patient. The person using the preassembled device 10 need not rearrange the parts in order to ensure that the bevel 74 is facing upwardly as generally desired. In some cases, a person may wish to insert the placement device 10 with the bevel 74 180° from that shown in FIG. 4, that is, with the bevel 74 facing downwardly. In such case, the needle introducer 14 may be removed from catheter 12, rotated 180° relative to the catheter, and then reinserted with the cantilever 72 again between the hub ears 22 and 24, but on the bottom side of the catheter.

The stabilizer 16 may be packaged with the catheter 12 and introducer 14, but not assembled on the catheter. In this way, the user can use the device 10 without the stabilizer if desired, or may readily assemble the stabilizer onto the catheter hub as previously mentioned. Since the stabilizer bore 44 is circumferentially continuous, the stabilizer cannot inadvertently come off of the catheter. Also, the stabilizer 16, since it is preferably formed of a relatively soft and pliable or supple material, is generally more comfortable to the patient than rigid ones, especially where the patient has to have the catheter 12 taped to the skin for an extended period of time.

The plug 58 may be formed, for example, of a porous hydrophobic plastic material having interconnecting pores. They are made to allow air to flow through it but prevent liquid from flowing through it at pressures encountered during venipuncture. Such plugs may be made by Glasrock Products, Inc., Porex Division, Fairburn, Georgia.

As various changes could be made in the above-described construction without departing from the scope of the invention, it is intended that all matter contained in the above description and shown in the accompanying drawings be interpreted as illustrative and not in a limiting sense.

I claim:

1. An intravenous catheter placement device comprising a catheter including a catheter hub having a relatively rigid proximal connector end portion for connecting the hub in fluid connection with another device, and a flexible cannula extending distally from the distal end of said catheter hub, said catheter hub having a frusto-conical portion intermediate the distal and proximal ends thereof and having an annular recess in the outer wall of said frusto-conical portion said recess having a distal wall and a proximal wall, said recess having first guide means thereon, and a catheter securing member of relatively resilient material having a hub portion and a pair of opposed wings integral with said hub portion, said securing member hub portion having having distal and proximal ends said securing member hub portion having an inner frusto-conical wall extending circumferentially continuously and having second guide means on the inner wall thereof complementary to said first guide means, said securing member being movable axially over said frusto-conical portion of said catheter hub and into said recess with said first and second guide means cooperating to orientate said wings in predetermined circumferential relation with said hub, the distal end of said securing member abutting the distal wall of the recess when the securing member is disposed in said recess to hold said securing member therein.

2. The device of claim 1 further including a catheter introducer comprising a needle hub, a needle having a beveled distal end connected to said needle hub with a predetermined orientation with respect to the needle hub, said needle being receivable in said cannula with said beveled distal end extending distally from the distal end of said cannula, said needle hub and said catheter hub having complementary orientation means cooperable to prevent relative rotation between said catheter and said introducer and predeterminately locate said bevel relative to said wings, said catheter hub orientation means including a pair of spaced, opposed luer lock ears predeminately located on said catheter hub adjacent the proximal end thereof, and said needle hub orientation means including cantilever means on said needle hub extending distally between said ears when said needle is received in said cannula to thereby predeterminately position said needle bevel with respect to said wings.

3. The device of claim 1 or 2 wherein said first guide means includes generally axially extending integral key means extending through said annular recess in the catheter hub, and said second guide means includes axially extending keyway means for receiving said key means during movement of said securing means into said recess.

4. The device of claim 1 wherein said securing member is of a relatively elastic plastic material and the inner diameter of the distal end of said hub portion of said securing means is less than the outer diameter of said catheter hub at the distal end of said recess to ensure against axial relative movement between said securing member and said catheter hub.

5. The device of claim 1 wherein said catheter hub includes slip resistant means in said recess adapted for grasping with fingers of the person using the device.

* * * * *